United States Patent [19]

Herweck et al.

[11] Patent Number: 5,197,976
[45] Date of Patent: Mar. 30, 1993

[54] MANUALLY SEPARABLE MULTI-LUMEN VASCULAR GRAFT

[75] Inventors: Steve A. Herweck, Nashua; Theodore Karwoski, Hollis; Paul Martakos, Pelham, all of N.H.

[73] Assignee: Atrium Medical Corporation, Hollis, N.H.

[21] Appl. No.: 760,716

[22] Filed: Sep. 16, 1991

[51] Int. Cl.$^5$ .............................................. A61F 2/04
[52] U.S. Cl. ........................................ 623/1; 623/11; 623/12
[58] Field of Search ............................ 623/1, 11, 12; 128/DIG. 14

[56] References Cited

U.S. PATENT DOCUMENTS 2,978,787  4/1961  Liebig .................................... 623/1
3,805,301  4/1974  Liebig .................................... 623/12

OTHER PUBLICATIONS

Campbell et al., "Expanded Polytetraflouro-Ethylene As A Small Artery Substitute", *Transactions A.S.A.I.O.*, vol. XX-A, Apr. 3-5, 1975, pp. 86-90.

*Primary Examiner*—David Isabella
*Assistant Examiner*—Debra S. Brittingham
*Attorney, Agent, or Firm*—Lahive & Cockfield

[57] ABSTRACT

A vascular prosthesis has a plurality of tubular structures, each of which is manually separable from the others. Each tube structure has a biocompatible exterior surface and a lumen of predetermine diameter. Fluid, such as blood, is channelled through the lumina upon implantation in an arterial or venous pathway. Each of the tube structures is separable from the others over at least a portion of the axial extent of the exterior surface.

25 Claims, 5 Drawing Sheets

MANUALLY SEPARABLE MULTI-LUMEN VASCULAR GRAFT

BACKGROUND OF THE INVENTION

One type of implantable device is a synthetic vascular graft such as is commonly used to replace damaged or dysfunctional arterial or venous pathways, for example at the site of an aneurysm or occlusion. Bypass grafts are often used to divert blood flow around damaged regions to restore blood flow. Another use of vascular prostheses is for creating a bypass shunt between an artery and vein, specifically for multiple needle access, such as is required for hemodialysis treatments. Following multiple percutaneous invasions into a vein, the vein may either collapse along the puncture track or become aneurysmal, leaky or fill with clot, causing significant risk of pulmonary embolization. Vascular prostheses have been used for many years as an alternative to patients' own veins for vascular access during hemodialysis.

Materials have been developed which exhibit the characteristics desirable for use in artificial prostheses. These characteristics include chemical inertness and resistance to undesirable physical changes in the medium of use. An example of such material is polytetrafluoroethylene (PTFE), a porous polymeric material which may be stretched to a specified length and thickness. When thus expanded, the material consists of a network of interrelated nodes and fibrils. The diameters of the fibers and the size of the pore vary depending on the stretching conditions. Since the porosity of the tubing can be varied, it is possible to adjust the porosity to minimize the occurrence of thrombosis. It is difficult, however, to elicit natural occlusion of suture holes in vascular prosthesis made of PTFE tubing alone, due to the relative elasticity of the porous PTFE tubing material.

Typically, PTFE vascular grafts cannot safely be used to withdraw blood until they have been in place for a minimum of 14 days after surgery and have become surrounded by fibrotic tissue, because of the bleeding which occurs at the site of a needle puncture in these grafts if fibrotic tissue is absent. Complications commonly encountered with early puncturing of PTFE arteriovenous fistulas include a hematoma surrounding the graft, false aneurysm, and graft occlusion. Other materials which have been used for vascular grafts include autologous saphenous vein, woven or knitted Dacron ® brand polyester, or other synthetic polyester fiber, microporous Teflon ®, modified bovine carotid xenograft, and modified human umbilical vein. None of these has overcome the problems with early puncture of the graft following implantation.

Another drawback of the vascular grafts described above is that after implantation they initially acquire a thin inner coating of thrombus, which is replaced to some extent by endothelium growing in from the end of the graft or from capillary tufts that penetrate the interstices of the graft. Thus, the degree of porosity is generally a compromise between the capacity of the particular graft to accommodate ingrowing connective tissue and capillary tufts, and excessive permeability to blood at the time of implantation.

In the course of replacing or by-passing damaged arteries and veins, the need often arises to have prosthetic devices of different diameters. In the physical setting, arteries are generally smaller in diameter than veins, thus requiring arterial and venous grafts to be available in a range of diameters. One way to provide grafts of different diameters to the surgeon at the time of implantation is to provide an array of individual vascular grafts each having a different diameter to the surgeon. These grafts are of a fine material, which can become entangled or torn during handling. In order to make these individual grafts communicate with each other, they must be sutured together.

It is therefore, an object of the invention to provide a vascular graft including at least two lumen-defining structures which can be manually separated from one another.

It is another object of the invention to provide such a graft wherein the lumina defined by the structures are of unequal diameters.

SUMMARY OF THE INVENTION

These and other objects are achieved by the present invention which features a vascular prosthesis comprising plural longitudinally parallel tube structures which are attached to one another over at least a portion of their longitudinal extent. Each of the tube structures comprises a wall defining a longitudinally extending biocompatible exterior surface and a lumen of predetermined diameter for channeling fluid flow therethrough. The parallel tube structures are attached to one another at their exterior surfaces. The prosthesis is formed to permit manual spatial separation of the tube structures. That is, the structures can be physically separated, at least partially, to form a branched tubular structure. For example, depending on the number of tube structures forming the prosthesis, therefore, a bifurcated trifurcated, or other branching tubular structure can be formed.

The lumen of each tube can differ in diameter to allow separation of the tubes into, e.g., arterial grafts and venous grafts having different diameters. The lumina can form separate and distinct flowthrough paths along the entire longitudinal extent of the prosthesis, or can join at one end to form a single lumen. Various embodiments of the invention can be adapted to optimize specific implant requirements.

In a preferred embodiment of the invention, the tube structures are manufactured from stretched and/or expanded polytetrafluoroethylene (PTFE) using a co-extrusion process. The structures can optionally include an identifying indicia, such as colored lines, to distinguish each structure from the others.

The present vascular graft has several advantages. For example, the amount of surgical time it takes to implant a vascular graft is determined, in part, by the amount of time it takes a surgeon to create each anastomosis. Using the device of the present invention, the number of anastomoses, thus surgery time, is reduced because the common end of the branches only has to be sutured once. That is, the graft of the present invention requires a single connection to a patient's vascular system for the terminal end, followed by a connection for each distal end. By contrast, using single stranded grafts, each graft requires at least two anastomoses, one at the point of origin and another at the point of insertion. The time saved by use of the present invention, therefore, can be significant.

In addition, the ability to implant multiple grafts with a single originating anastomosis allows surgeons to effectively perform multiple grafts which mimic the branching of the natural vascular pathway using the inventive prosthetic device. Thus, the present invention allows a branched arterial or venous graft to be implanted without the necessity of suturing two grafts together. In various other embodiments of the invention, the structure can be formed so that the various lumina have specific diameters, and so that the degree of separation of the tubular structure can be limited.

BRIEF DESCRIPTION OF THE DRAWINGS

The foregoing and other objects of this invention, the various features thereof, as well as the invention itself, may be more fully understood from the following description, when read together with the accompanying drawings in which.

Like reference characters in the respective figures indicate corresponding parts.

DETAILED DESCRIPTION OF THE INVENTION

Figure 1:
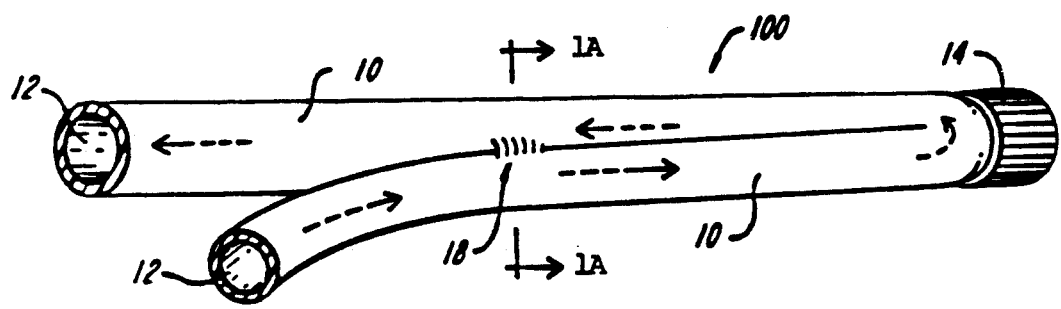
FIG. 1 is a schematic perspective view of a bilumenal separable vascular prosthesis with a cap at one end.

The invention features a vascular prosthesis including two or more tube structures defining lumina of various diameters for accomodating the flow of fluid, such as blood, therethrough. Each of the tube structures is manually separable from the others during surgical introduction of each prosthesis, to allow each tube structure to be used as a separate prosthesis at different vascular sites.

In addition to use as a vascular graft, it is also possible to utilize one of the lumina for fluid flow of a different nature, or as a vehicle for drug delivery. The materials used in the construction of the tube structures can be semi-permeable to agents of specific sizes to allow communication of the fluid or drug with the blood flow of an adjacent tube structure. A multi-lumenal vascular graft having drug delivery capability is described in detail in co-pending U.S. application Ser. No. 760,753, Implantable Prosthetic Device For The Delivery of A Bioactive Material Ser. No. 760,653 filed concurrently herewith, the teachings of which are hereby incorporated herein by reference. To prevent osmosis of the agent from the filled lumen to the surrounding tissue, the external surface of the tube structures, or the internal walls surrounding the lumina, can be coated with a non-permeable, biocompatible material.

The internal diameter (ID) of each lumen depends upon the intended use for each tube structure. In general, lumina having ID's of from about 3 mm to about 24 mm are useful as vascular grafts. For example, a tube structure intended for insertion in an arterial pathway can have a lumen ID of from about 6 mm to about 18 mm. A tube structure for insertion in a venous pathway can have a lumen ID of from about 12 mm to about 24 mm. The lumina can each have the same or different diameters for insertion into one or more types of pathways. For example, the lumen ID of tube structures to be used as arterial grafts is generally less than the ID lumen for use in venous grafts.

The outer diameter (OD) of the tube structures is generally not related to the internal lumen diameter. For example, in an embodiment of the invention having two tube structures, the external diameter of both tube structures can be the same, while the internal lumen diameter of each tube differs.

The thickness of the lumen walls will vary depending on the type of vascular graft. Generally, an arterial graft will require thicker walls than a venous graft. However, the exact dimensions will depend on the specific purpose. For manufacturing purposes, the die used for extrusion may be varied to achieve walls having desired thicknesses. Wall thicknesses of from about 0.1 mm to about 1.2 mm are generally useful for vascular graft applications.

The tube structures are joined by a wall which allows them to be easily separated. In various embodiments of the invention, the tube structures are separated either by pulling them apart or by cutting them with scalpel or scissors. To facilitate separation of the tube structures are joined by a small bead or seam of material. The bead or seam serves to hold the tubes together while allowing them to be pulled or cut apart. In another embodiment, the tubes are joined by a thickened wall portion which, when separated, forms two walls so that separated tube structures have walls of substantially equal thickness.

In another embodiment of the invention, one or more of the tube structures can include identifying markings. These markings can be in the form of lines, dots, or any other designs which run along the entire or partial length of the exterior surface of each tube structure. These markings can be used to distinguish tube structures of different dimensions, and/or to allow the user to trace each tube structure should it become twisted during use. The identification markings allow the surgeon, or other user of the invention, to implant the structure at one point along the arteriovenous pathway, then thread it to a distal point while at the same time being able to distinguish one tube structure from the others.

For example, the point of origin for the venous graft may be in the greater saphenous vein, another graft may originate in the adjacent femoral artery, and the point of insertion for the structure is the anterior tibial vein and artery, respectively. In traversing the patient's leg, it would be easy for a surgeon to twist or otherwise lose track of which structure involved venous bloodflow and which structure transported oxygenated blood. Thus, labelling the exterior surfaces of at least one of the tube structures would facilitate user distinction between the structures, reducing the risk of error and extended surgical time.

In another embodiment of the present invention, the lumen walls can be pretreated with an agent to reduce the risk of occlusion of the graft. For example, glow discharge coatings and plasma polymerization methods such as are taught by U.S. Pat. No. 4,632,842 to Karwoski et al., reduce or prevent smooth muscle cell build-up within the lumen. The walls can also be precoated, for example, with a gelatin or a "time-release" agent e.g., a material that releases small, localized amount of anticoagulant, to the graft site.

The present tubular devices can be manufactured from various biocompatible material. For example, Teflon ® brand polytetrafluoroethylene (PTFE), both expanded and unexpanded, is suitable for use with the invention. Polymer alloys are suitable as well. Dacron ® brand polyester fiber, mandrel spun polyurethane, and silicone elastomer fibers are also well suited for use with the invention. Moreover, copolymeric materials such as described in U.S. Pat. Nos. 4,187,390 and 4,973,609 can be utilized. These are materials made up of more than one type of monomer and have advantages, as described in the cited patents, in some applications. In a preferred embodiment, the tube structures are manufactured from (PTFE) which has been stretched and/or expanded as described in further detail below.

As stated, in a preferred embodiment, the inventive prosthesis is manufactured by paste forming and stretching and/or expanding highly crystalline, unsintered, polytetrafluoroethylene. Paste forming by extrusion of PTFE is well-known in the art. Generally, the steps in paste-forming include mixing the resin with a lubricant, such as odorless mineral spirits, and then forming the resin, such as by extrusion, into shaped articles. The lubricant is removed from the formed article by drying, following which the article is sintered by its being heated above its crystalline melting point of approximately 327° C. The sintered, unexpanded, article is a relatively impermeable product. To achieve a greater degree of permeability in the finished product, however, the prostheses of the invention can be further treated prior to sintering.

Paste-formed, dried, unsintered, shapes can be further treated by expanding and/or stretching them in one or more directions under certain conditions so that they become porous yet retain their strength. Such stretching and expansion with increased strength occurs with certain preferred tetrafluoroethylene resins, e.g., PTFE. The porosity of the material is affected by the temperature and rate at which it is stretched and expanded. A method for manufacturing porous PTFE tubing appropriate for use in the present invention is described in detail, for example, in U.S. Pat. No. 3,953,566, and U.S. Pat. No. 4,973,609 the teachings of both of which are hereby incorporated by reference herein.

Stretched and expanded PTFE is characterized by a microstructure of nodes interconnected by small fibrils. The space between the nodes and the number of fibrils is controlled by changes in the temperature and rate of stretching and expansion of the PTFE, to produce tubing having predetermined porosity and flex qualities. For example, products which are stretched and expanded at high temperatures and high rates have a more homogeneous structure, i.e., they have smaller, more closely spaced nodes, which nodes are interconnected with a greater number of fibrils. While the resulting structure is stronger than products stretched and expanded at lower temperatures and rates, the porosity is also reduced. Thus, by controlling these two factors, it is possible to construct a series of tube structures having a range of porosity within a desirable range of strength.

It has been noted that when tube structures manufactured as described above are heated to above the lowest crystalline melting point of the PTFE, disorder begins to occur in the geometric order of the crystallites and the crystallinity of the structure decreases, with concomitant increase in the amorphous content of the polymer. These amorphous regions within the crystalline structure appear to greatly inhibit slippage along the crystalline axis of the crystallite, and to lock fibrils and crystallites so that they resist slippage under stress. Therefore, the heat treatment may be considered an amorphous locking process. Amorphous locking results in an increase in amorphous content, regardless of the crystallinity of the starting resins. The heat treatment above 327° C. therefore causes an increase in strength in the tube structures, which can be double that of non-heat-treated material.

The upper melting range of PTFE is approximately 345° C., thus heat treatment is more effective above this temperature. Lower temperatures can be used to obtain the same results if exposure time is increased commensurately. The optimum heat treating temperature is in the range of from about 350° C. to about 370° C., with heating periods in the range of from about five seconds to about one hour. The increase in strength of the polymer matrix is dependent upon the strength of the extruded material before expansion, the degree of crystallinity of the polymer, the rate and temperature at which the expansion is performed, and amphorous locking.

Referring to the Figures, one embodiment of the device is shown in FIG. 1, in which the tube structures 10 is joined at one end by a terminal cap assembly 14 with fluid flow through each lumen 12. The tube structures 10 can include a notch near the fused, terminal end of the structures 10 to direct fluid flow through each lumen. The terminal cap assembly 14 can be made of any suitable biocompatible material. The terminal cap assembly 14 can optionally be removable to facilitate certain procedures, e.g., thrombectomy. In that example, an incision is made away from the anastoma and needle access area, thereby allowing the clot to be removed without disrupting the intact graft and flood flow through the lumina.

Figure 1A:
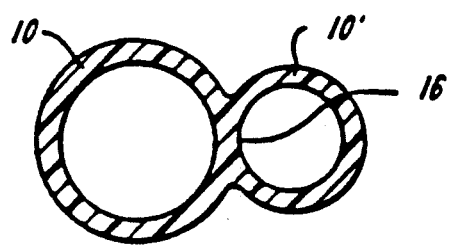
FIG. 1A is a schematic cross-section of the embodiment shown in FIG. 1 taken along axis A—A.

In the embodiment shown in FIG. 1A, the tube structures 10 share a divisible wall structure 16 which has a thickness sufficient to allow a user of the apparatus 100 to tear one tube structure 10 apart from another 10' without affecting the integrity of either tube structure. The tube structures can optionally include a built-in stop-gap 18, which prevents a user from dividing the tube structures beyond the point of structural integrity.

Figure 2:
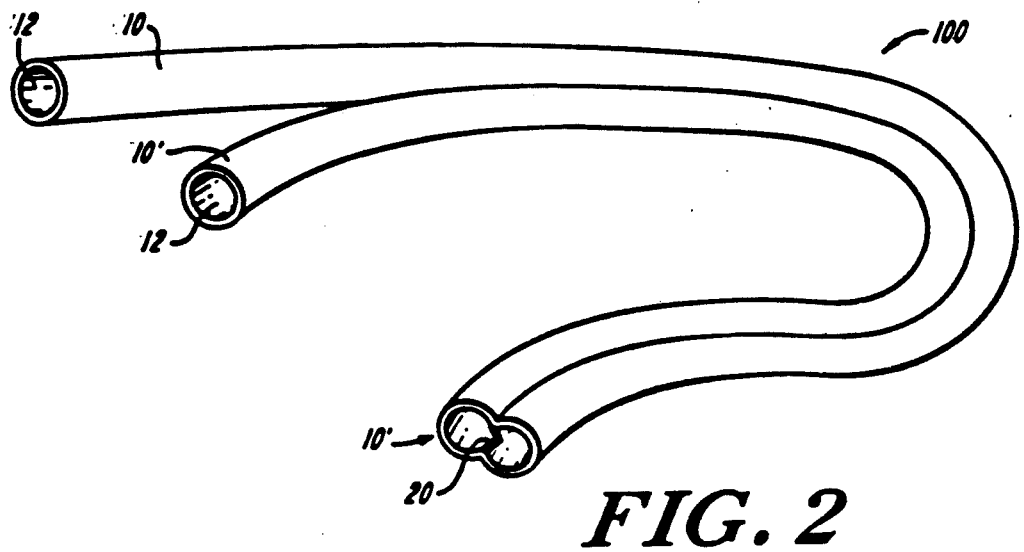
FIG. 2 is a schematic perspective view of a bilumenal, separable prosthesis.

The device 10 can be straight, and relatively rigid, as shown, by example, in FIG. 1, or can be flexible for configuration in a variety of functional modes, as shown, by example, in FIG. 2. In that embodiment, the device 100 includes two separable tube structures 10, 10' of relatively flexible structure which can be used for multiple arteriovenous applications. In the embodiment shown in FIG. 2, the two lumina 12 are of the same diameter for use as a multiple vein return to relieve, for example, arterial steal syndrome.

Figure 2A:
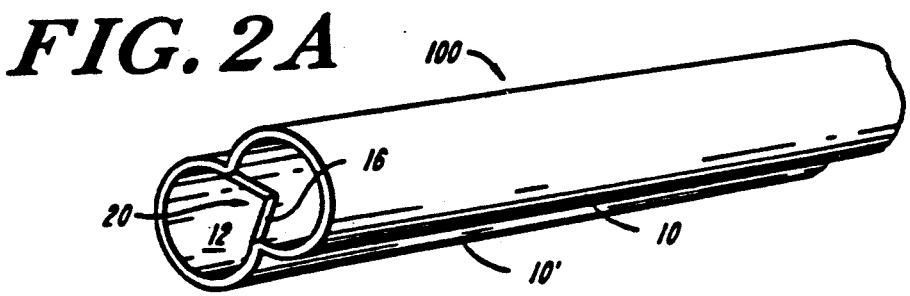
FIG. 2A is a schematic, enlarged perspective view of the notched end of the embodiment of FIG. 2.
Figure 4:
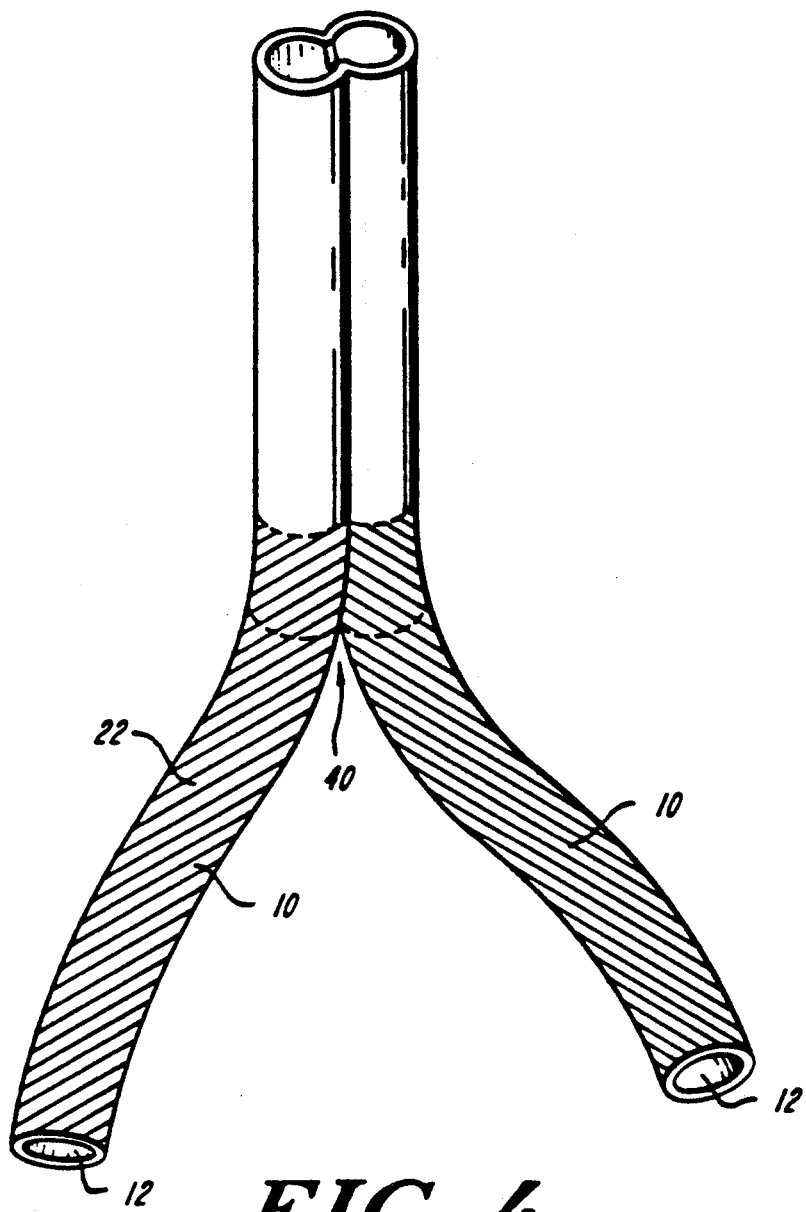
FIG. 4 is a schematic perspective view of a bilumenal, separable, vascular prosthesis.

As illustrated in FIG. 2A, the device can include a divider notch 20 to direct blood flow through the lumina 12 and 12'. The notches can have various configurations, including a V-shaped notch, a rounded notch, or other configurations as may be desirable based on the specific location of the prosthesis and the type of fluid flow desired by the user.

Figure 3:
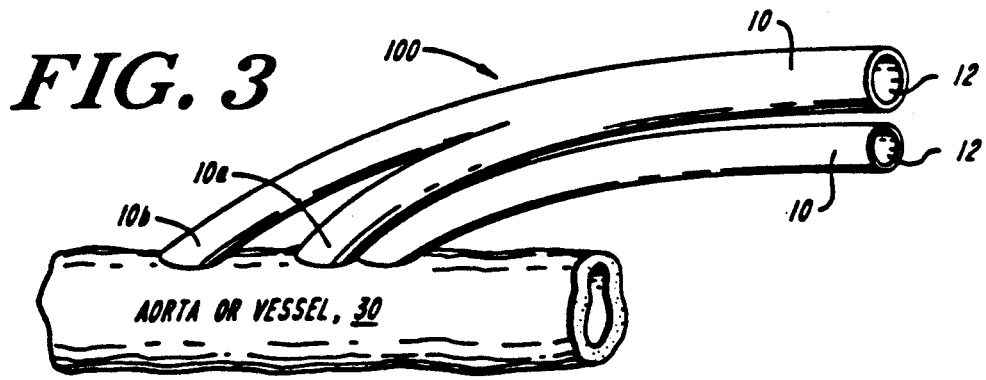
FIG. 3 is a schematic perspective view of a bilumenal prosthesis attached to a blood vessel.

Another embodiment of the present invention is illustrated in FIG. 3. In that embodiment, the device 100 includes pre-divided tube structures 10a and, 10b at the terminal end instead of a terminal end cap. This embodiment of the invention can be used to graft two or more vessels 30 to feed into one or more lumina.

Figure 5:
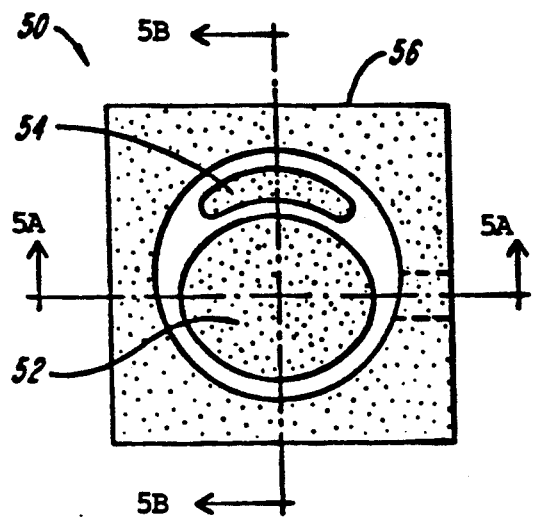
FIG. 5 is a schematic front elevation view of a die used to manufacture the embodiment of FIG. 1.
Figure 5B:
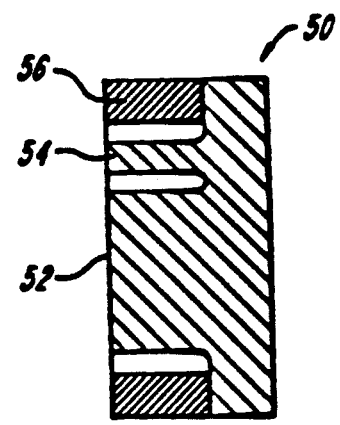
FIGS. 5A-5B are cross-sections of the die of FIG. 5, taken along axis A—A and B—B, respectively.
Figure 5A:
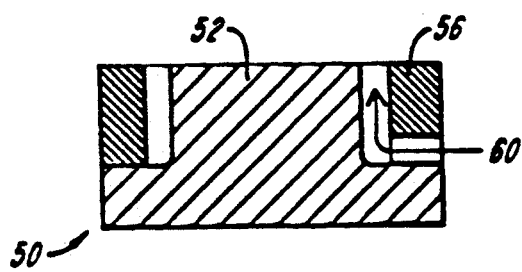

The extrusion can be performed using dies of predetermined shape of the type known in the art. FIGS. 5, and 5A-5B show cross-section views of an exemplary die which can be used in the manufacture of a device of the present invention.

Generally, and as illustrated, the die 50 consists of a peripheral support structure 56 encasing a first solid die-piece 52 for forming a first lumen, and second solid die-piece 54 proximal to the first die-piece 52 for forming a secondary lumen. The specific spacing of the first die-piece 52 from the second die-piece 54 depends upon the specific desired prosthesis configuration. As best shown in the cross-section in FIG. 5A, the die 50 may include an external port 60 for introduction of PTFE paste, or the like, for extrusion. FIG. 5B shows in cross-section the exemplary die 50 of FIG. 5, showing aperture 58 for forming membrane (18 of FIG. 1) of the invention. The manufacture of such dies is understood to be well known in the art.

After the PTFE resin is formed, such as by extrusion as discussed above, it is stretched and/or expanded and then sintered while being held in the stretched and/or expanded state. Stretching refers to elongation of formed resin while expansion refers to enlargement of the formed resin perpendicularly to its longitudinal axis. The rate of stretching and the stretch ratio affect the porosity of the finished product in a predictable manner allowing a prosthetic device to be produced having a specified porosity. The rate of stretching refers to the percentage of elongation per second that the resin is stretched while the stretch ratio refers to the relationship between the final length of the stretched resin and the initial length of the stretched resin. For example, stretching an extruded PTFE tube at a stretch ratio of two to one and a stretch rate of sixty results in a porosity of approximately forty. This porosity is unitless and is determined as set forth on page eighty-four of the American Society For Testing of Materials' Special Technical Publication Number 898. So, for example, based on stretch ratios ranging from two to one, to six to one, a stretch rate of sixty percent per second yields a porosity of between approximately forty and approximately ninety, a stretch rate of one hundred and forty percent per second yields a porosity of between approximately sixty and approximately eighty-five, and a stretch rate of nine hundred percent per second yields a porosity of between approximately sixty-five and approximately eighty-five.

In addition to the porosity, the geometry of the node and fibril network of PTFE can be controlled during stretching and expansion. In the case of uniaxial stretching, that is, elongation of the formed PTFE resin along the direction of extrusion, the nodes are elongated causing the longer axis of each node to be oriented perpendicularly to the direction of stretch. Accordingly, the fibrils are oriented parallel to the direction of stretch. Biaxial stretching, additionally includes expanding the PTFE resin in the radial direction and can be utilized to produce a prosthetic device having a composite porosity. As in uniaxial stretching, the rate and ratio of radial expansion affects the resulting porosity of the prosthetic device.

Figure 6:
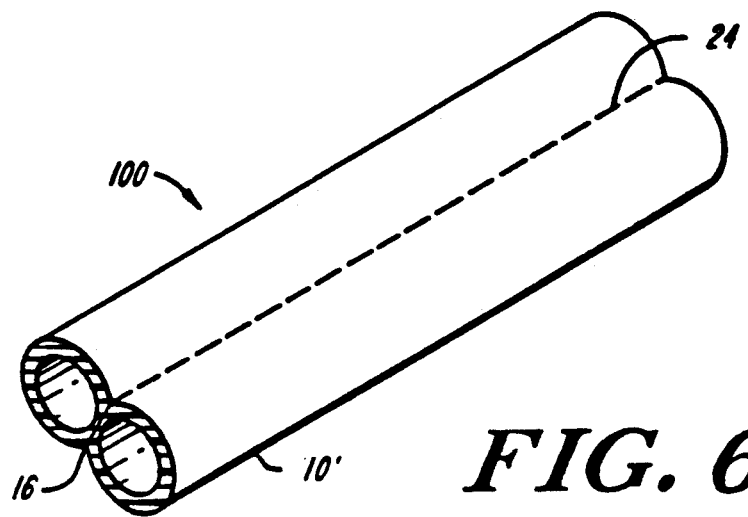
FIGS. 6-6A are schematic showing a representative diluminal prosthesis with a perforated divisible wall between the tubes.
Figure 6A:
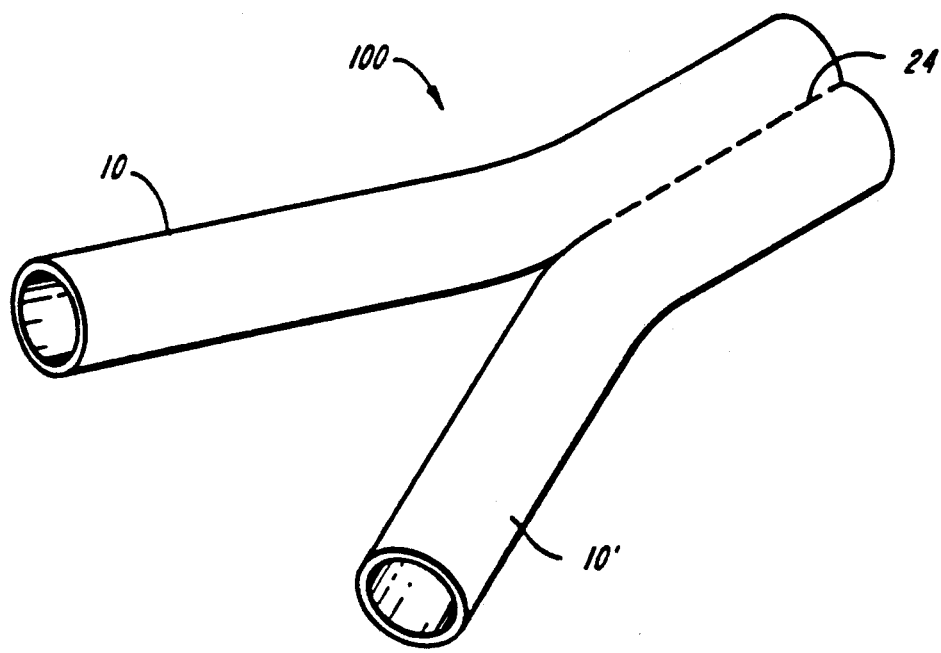

Another embodiment of the invention is illustrated in FIGS. 6 and 6A. FIG. 6 shows a diluminal structure 100 having tube structures 10 and 10' joined by a divisible wall 16 which has perforations 24 therein to facilitate separation of the tubes 10 and 10'. FIG. 6A shows tubes 10 and 10' partially separated.

In another aspect of the invention, the tube structures can be formed using other paste-forming operations known to those skilled in the art, for example, any of the available molding processes. Paste-forming resins other than PTFE, as discussed above, may also be used which are generally formable into such tube structures, and which may result in relatively fluid impermeable structures. Due to the physiological properties of the arteriovascular system, it is important for the tube structures to be gas permeable, or selectively gas permeable, to permit oxygen-carbon dioxide exchange. However, gas impermeable tube structures are useful as vascular grafts in some applications.

In operation, the surgeon surgically exposes the desired region for introduction of the vascular prosthesis of the invention. The desired site may be an area of occlusion or weakness in the patient's arteriovascular system, for example. An interruption of the patient's blood flow is performed, and the surgeon manually separates the tube structures from each other, tearing along the common wall to the desired stop point. Thus, a single divided vascular prosthesis is surgically implanted and sutured or otherwise secured in the desired location. Proper positioning of the prosthesis requires alignment of the lumen with the appropriate blood flow pathway such that the patient's blood flow is diverted through a lumen of the prosthesis. The same procedure is then repeated for the other lumina of the prosthesis, or the extra lumen can be tied off and remain unused.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An implantable vascular prosthesis comprising plural longitudinally parallel tube structures, each of said tube structures comprising a wall defining a longitudinally extending biocompatible exterior surface and an interior lumen of predetermined diameter for channeling fluid flow therethrough, said parallel tube structures being releasably connected to one another via a thickened wall portion extending over at least a portion of the longitudinal extent of said exterior surfaces to permit manual spatial separation of said tube structures.

2. The vascular prosthesis of claim 1, wherein said tube structures consist of polytetrafluoroethylene.

3. The vascular prosthesis of claim 2, wherein said polytetrafluoroethylene is selected from the group consisting of, expanded polytetrafluoroethylene, stretched polytetrafluoroethylene, and stretched and expanded polytetrafluoroethylene.

4. The vascular prosthesis of claim 1, wherein said tube structures consist of copolymeric material.

5. The vascular prosthesis of claim 1, wherein said tube structures include identifying indicia for distinguishing each of said structures from the other of said structures.

6. An implantable vascular prosthesis comprising first and second longitudinally parallel tube structures, each of said structures comprising a wall consisting of polytetrafluoroethylene and defining a longitudinally extending biocompatible exterior surface and an interior lumen of predetermined diameter for channeling blood flow therethrough, said lumina being of unequal diameters and converging to form a single lumen at one end of the vascular prosthesis, said tube structures being releasably connected to one another over at least a portion of the longitudinal extent of said exterior surfaces to permit manual spatial separation of said tube structures.

7. The vascular prosthesis of claim 6, wherein said tube structures are attached to one another via a thickened wall portion.

8. The vascular prosthesis of claim 6, wherein said tube structures are attached to one another via a bead of material.

9. The device of claim 6 wherein said polytetrafluoroethylene is selected from the group consisting of, expanded polytetrafluoroethylene, stretched polytetrafluoroethylene, and stretched and expanded polytetrafluoroethylene.

10. The vascular prosthesis of claim 6, wherein said tube structures consist of a copolymeric material.

11. The vascular prosthesis of claim 6, wherein said tube structures include identifying indicia for distinguishing each of said structures from the other of said structures.

12. An implantable vascular prosthesis comprising plural longitudinally parallel tube structures, each of said tube structures comprising a wall defining a longitudinally extending biocompatible exterior surface and an interior lumen of predetermined diameter for channeling fluid flow therethrough, said parallel tube structures being releasably connected to one another via a bead of material extending over at least a portion of the longitudinal extent of said exterior surfaces to permit manual spatial separation of said tube structures.

13. The vascular prosthesis of claim 12, wherein said tube structures consist of polytetrafluoroethylene.

14. The vascular prosthesis of claim 13, wherein said polytetrafluoroethylene is selected from the group consisting of, expanded polytetrafluoroethylene, stretched polytetrafluoroethylene, and stretched and expanded polytetrafluoroethylene.

15. The vascular prosthesis of claim 12, wherein said tube structure consist of a copolymeric material.

16. The vascular prosthesis of claim 12, wherein said tube structures include identifying indicia for distinguishing each of said structures from the other of said structures.

17. An implantable vascular prosthesis comprising plural longitudinally parallel tube structures, each of said tube structures comprising a wall defining a longitudinally extending biocompatible exterior surface and an interior lumen of predetermined diameter for channeling fluid flow therethrough, said parallel tube structures being releasably connected to one another over at least a portion of the longitudinal extent of said exterior surfaces to permit manual spatial separation of said tube structures wherein the diameter of the lumen of one of the plural tube structures is different from the diameter of the lumen of at least one other of the plural tube structures.

18. The vascular prosthesis of claim 17, wherein said tube structures consist of polytetrafluoroethylene.

19. The vascular prosthesis of claim 18, wherein said polytetrafluoroethylene is selected from the group consisting of, expanded polytetrafluoroethylene, stretched polytetrafluoroethylene, and stretched and expanded polytetrafluoroethylene.

20. The vascular prosthesis of claim 17, wherein said tube structures consist of a copolymeric material.

21. An implantable vascular prosthesis comprising plural longitudinally parallel tube structures, each of said tube structures comprising a wall defining a longitudinally extending biocompatible exterior surface and an interior lumen of predetermined diameter for channeling fluid flow therethrough, said parallel tube structures being releasably connected to one another over at least a portion of the longitudinal extent of said exterior surfaces to permit manual spatial separation of said tube structures wherein at least two of the lumina converge to form a single lumen at one end of said tube structure.

22. The vascular prosthesis of claim 21, wherein said tube structures consist of polytetrafluoroethylene.

23. The vascular prosthesis of claim 22, wherein said polytetrafluoroethylene is selected from the group consisting of, expanded polytetrafluoroethylene, stretched polytetrafluoroethylene, and stretched and expanded polytetrafluoroethylene.

24. The vascular prosthesis of claim 21, wherein said tube structures consist of a copolymeric material.

25. The vascular prosthesis of claim 21, wherein said tube structures include identifying indicia for distinguishing each of said structures from the other of said structures.

* * * * *